United States Patent
Bunick et al.

(10) Patent No.: US 6,814,978 B2
(45) Date of Patent: Nov. 9, 2004

(54) PROCESS FOR PREPARING A SOFT TABLET

(75) Inventors: Frank J. Bunick, Randolph, NJ (US); Joseph Luber, Quakertown, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 240 days.

(21) Appl. No.: 09/752,601

(22) Filed: Dec. 29, 2000

(65) Prior Publication Data

US 2002/0122822 A1 Sep. 5, 2002

(51) Int. Cl.⁷ .................................................. A61K 9/20
(52) U.S. Cl. ...................... 424/464; 424/441; 424/465; 514/770; 514/778; 514/779; 514/781; 514/772.3
(58) Field of Search ................................ 424/441, 464, 424/465

(56) References Cited

U.S. PATENT DOCUMENTS

| | | | |
|---|---|---|---|
| 4,327,076 A | * | 4/1982 | Puglia et al. .................. 424/38 |
| 4,642,903 A | | 2/1987 | Davies |
| 5,178,878 A | | 1/1993 | Wehling et al. |
| 5,223,264 A | | 6/1993 | Wehling et al. |
| 5,464,632 A | | 11/1995 | Cousin et al. |
| 5,503,846 A | | 4/1996 | Wehling et al. |
| 5,631,023 A | | 5/1997 | Kearney et al. |
| 5,729,958 A | | 3/1998 | Kearney et al. |
| 5,738,875 A | | 4/1998 | Yarwood et al. |
| 5,827,541 A | | 10/1998 | Yarwood et al. |
| 5,837,287 A | | 11/1998 | Yarwood et al. |
| 5,976,577 A | | 11/1999 | Green et al. |
| 6,024,981 A | | 2/2000 | Khankari et al. |
| 6,106,861 A | | 8/2000 | Chauveau et al. |
| 6,270,807 B1 | * | 8/2001 | Danielson et al. .......... 424/497 |
| 6,316,026 B1 | | 11/2001 | Tatara et al. |
| 6,596,311 B1 | | 7/2003 | Dobetti |

FOREIGN PATENT DOCUMENTS

WO          99/47126          9/1999

* cited by examiner

Primary Examiner—James M. Spear

(57) ABSTRACT

The invention relates to a process for preparing a soft tablet capable of being chewed or disintegrated in the oral cavity. The tablet is prepared by forming a tablet having a friability of less than about 2% from a mixture comprising a pharmaceutically active ingredient, an excipient in the form of a hydrate, and a water-swellable excipient, and then applying sufficient energy, preferably in the form of heat, to the tablet for a sufficient time to decrease the hardness of the tablet by at least about 20%.

14 Claims, No Drawings

PROCESS FOR PREPARING A SOFT TABLET

The present invention relates to a chewable or disintegrative tablet prepared by forming a tablet having a friability of less than about 2% from a mixture comprising a pharmaceutically active ingredient, an excipient in the form of a hydrate, and a water-swellable excipient, and then applying sufficient energy to the tablet for a sufficient time to decrease the hardness of the tablet by at least about 20%.

BACKGROUND OF THE INVENTION

Pharmaceuticals intended for oral administration are typically provided in solid form as tablets, capsules, pills, lozenges, or granules. Tablets are swallowed whole, chewed in the mouth, or dissolved in the oral cavity. Chewable or disintegrative tablets are often employed in the administration of pharmaceuticals where it is impractical to provide a tablet for swallowing whole, for instance with pediatric patients. In addition, with chewable tablets, the act of chewing helps to break up the tablet particles as the tablet disintegrates and may increase the rate of absorption by the digestive tract.

Several workers in the field have explored rapidly disintegrative tablets. For example, U.S. Pat. No. 6,106,861 relates to a rapidly disintegrative tablet comprising an excipient and an active ingredient in the form of microcrystals coated with a coating agent. The excipient comprises at least one disintegration agent, which may be crospovidone or croscarmellose, and a soluble diluent agent that is a polyol either in directly compressible form or in powder form. The polyol is selected from the group consisting of mannitol, xylitol, sorbitol, and maltitol.

U.S. Pat. No. 5,464,632 describes another rapidly disintegrative tablet, the excipient mixture of which is suitable for imparting a very short disintegration time in the mouth. The excipient mixture comprises one or more disintegrating agents of the carboxymethylcellulose type or insoluble reticulated PVP type, one or more swelling agents, and possibly a direct compression sugar such as dextrose.

U.S. Pat. No. 6,024,981 relates to a hard tablet that can be stored, packaged and processed in bulk, but dissolves rapidly in the mouth. The tablet comprises an active ingredient mixed into a matrix of a non-direct compression filler and a lubricant.

PCT Application No. WO 99/47126 discloses compressed tablets capable of rapidly dissolving in aqueous solutions, comprising at least one non-saccharide water soluble polymer such as polyvinylpyrrolidone, optionally a saccharide of low moldability such as glucose, optionally a saccharide of high moldability such as maltose, sorbitol or a mixture thereof, and optionally a sweetener such as sucralose. These tablets are prepared by wet granulation, specifically a) granulating a formulation comprising the non-saccharide, water soluble polymer and active ingredient using no organic solvents, (b) compressing this into tablet form, (c) humidifying the tablet by exposing it to an aerated environment having at least about 50 to 100% relative humidity, and (d) drying the tablet. The object of PCT Application No. WO 99/47126 is to form a hard tablet.

Applicants have now discovered that a soft, chewable or disintegrative tablet may be prepared from a mixture comprising a pharmaceutically active ingredient, an excipient in the form of a hydrate, and a water-swellable excipient. A tablet having a friability of less than about 2% is first produced, preferably by direct compression, and then subjected to sufficient energy for a sufficient amount of time to decrease the hardness of the tablet by at least about 20%. In a preferred embodiment, the tablet is packaged after the tableting step but before the application of energy. Prior to the application of energy, the tablet is sufficiently hard to withstand handling and packaging operations, and is softened only after it is in its package. The final product delivered to the consumer is a soft tablet capable of being chewed or disintegrated in the mouth before swallowing.

SUMMARY OF THE INVENTION

The present invention provides a process for preparing a chewable or disintegrative tablet, comprising forming a tablet having a friability of less than about 2% from a mixture comprising a pharmaceutically active ingredient, an excipient in the form of a hydrate, and a water-swellable excipient, and then applying sufficient energy to the tablet for a sufficient time to decrease the hardness of the tablet by at least about 20%.

The invention also provides a tablet capable of being chewed or disintegrated in the oral cavity prior to swallowing, comprising a) a pharmaceutically active ingredient, b) an excipient at least partially in the form of a hydrate, and c) a water-swellable excipient that is at least partially hydrated.

DETAILED DESCRIPTION OF THE INVENTION

In the first step of the process of the invention, a tablet is made from a mixture comprising one or more active ingredients, one or more excipients in the form of a hydrate and one or more water-swellable excipients.

Suitable active ingredients include pharmaceuticals, minerals, vitamins and other nutraceuticals. Suitable pharmaceuticals include analgesics, decongestants, expectorants, antitussives, antihistamines, gastrointestinal agents, diuretics, bronchodilators, sleep-inducing agents and mixtures thereof. Preferred pharmaceuticals for use as the active ingredient include acetaminophen, ibuprofen, flurbiprofen, ketoprofen, naproxen, diclofenac, aspirin, pseudoephedrine, phenylpropanolamine, chlorpheniramine maleate, dextromethorphan, diphenhydramine, famotidine, loperamide, ranitidine, cimetidine, astemizole, terfenadine, fexofenadine, loratadine, cetirizine, antacids, mixtures thereof and pharmaceutically acceptable salts thereof. More preferably, the active ingredient is selected from the group consisting of acetaminophen, ibuprofen, pseudoephedrine, dextromethorphan, diphenhydramine, chlorpheniramine, calcium carbonate, magnesium hydroxide, magnesium carbonate, magnesium oxide, aluminum hydroxide, mixtures thereof, and pharmaceutically acceptable salts thereof The active ingredient(s) are present in the tablet in a therapeutically effective amount, which is an amount that produces the desired therapeutic response upon oral administration and can be readily determined by one skilled in the art. In determining such amounts, the particular active ingredient being administered, the bioavailability characteristics of the active ingredient, the dose regime, the age and weight of the patient, and other factors must be considered, as known in the art.

If the active ingredient has an objectionable taste, it may be coated with a taste masking coating, as known in the art. Examples of suitable taste masking coatings are described in U.S. Pat. Nos. 4,851,226, 5,075,114, and 5,489,436. Commercially available taste masked active ingredients may also be employed. For example, acetaminophen particles which are encapsulated with ethylcellulose or other polymers by a coaccervation process may be used in the present invention. Coaccervation-encapsulated acetaminophen may be purchased commercially from Eurand America, Inc. Vandalia, Ohio, or from Circa Inc., Dayton, Ohio.

The excipient in the form of a hydrate may be selected from organic compounds such as dextrose monohydrate, maltodextrin, lactose monohydrate, dextrin, and citric acid monohydrate, as well as inorganic compounds including dibasic calcium phosphate dihydrate, dibasic sodium phosphate dihydrate, dibasic sodium phosphate heptahydrate, dibasic sodium phosphate dodecahydrate, monobasic sodium phosphate monohydrate, and monobasic sodium phosphate dihydrate. Preferably, the excipient in the form of a hydrate is an organic compound, more preferably dextrose monohydrate.

In a preferred embodiment, the excipient in the form of a hydrate also functions as a direct compression filler, and in particular is directly compressible dextrose monohydrate. Preferably, the directly compressible dextrose monohydrate has an average particle diameter of about 80 to about 500 microns, more preferably about 100 to about 400 microns.

The tablet preferably contains about 5 to about 90, more preferably about 15 to about 75, percent by weight of the excipient in the form of a hydrate, based on the total weight of the tablet.

The water-swellable excipient may be selected from superdisintegrants such as crospovidone, croscarmellose, sodium starch glycolate, cellulose compounds such as microcrystalline cellulose, starches, alginic acid and inorganic clays such as bentonite, attapulgite, and magnesium aluminum silicate. Preferably, the water-swellable excipient is crospovidone. Preferably, the water-swellable excipient is not water-soluble.

The amount of water-swellable excipient in the tablet is preferably about 0.1 to about 5 percent by weight, more preferably about 0.5 to about 3 percent by weight of the total weight of the tablet.

Preferably the excipient in the form of a hydrate is present in a higher amount than the water-swellable excipient. The preferred ratio of excipient in the form of a hydrate to water-swellable excipient in the tablet is from about 1:1 to about 150:1, more preferably from about 25:1 to about 75:1.

The tablet may contain other conventional ingredients, including other fillers, which include water-soluble compressible carbohydrates such as dextrose, sucrose, mannitol, sorbitol, maltitol, xylitol, lactose, and mixtures thereof; other conventional dry binders like polyvinyl pyrrolidone and the like; sweeteners such as aspartame, acesulfame potassium, sucralose, and saccharin; and lubricants, such as magnesium stearate, stearic acid, talc, and waxes. The mixture may also incorporate pharmaceutically acceptable adjuvants, including, for example, preservatives, flavors, antioxidants, surfactants, and coloring agents.

The tablet may be made in any manner, and a variety of tableting methods are known in the art. Conventional methods for tablet production include direct compression ("dry blending"), dry granulation followed by compression, and wet granulation followed by drying and compression. Other methods include the use of compacting roller technology such as a chilsonator or drop roller, or molding, casting, or extrusion technologies. All of these methods are well known in the art, and are described in detail in, for example, Lachman, et al., *The Theory and Practice of Industrial Pharmacy*, Chapter 11, ($3^{rd}$ Ed. 1986). Preferably the tablets are formed by the direct compression method, which involves directly compacting a blend of the active ingredient, the excipient in the form of a hydrate, the water-swellable excipient, and any other appropriate optional ingredients. After blending, a pre-determined volume of particles is filled into a die cavity of a rotary tablet press, which continuously rotates as part of a "die table" from the filling position to a compaction position. The particles are compacted between an upper punch and a lower punch to an ejection position, at which the resulting tablet is pushed from the die cavity by the lower punch and guided to an ejection chute by a stationary "take-off" bar.

Tableting should be carried out such that the tablet has a friability of less than about 2%, preferably less than about 1%, more preferably less than about 0.5%, prior to the application of energy to the tablet, which is the second step of the process. A discussion of tablet friability is presented in USP 23 (1995) 1216, p. 1981. Preferably, the tablet is also relatively hard after tableting. The hardness of the tablet prior to the application of energy is preferably at least about 3 kiloponds per square centimeter ($kp/cm^2$), more preferably at least about 5 $kp/cm^2$, most preferably at least about 6 $kp/cm^2$. Hardness is a term used in the art to describe the diametral breaking strength as measured by conventional pharmaceutical hardness testing equipment, such as a Schleuniger Hardness Tester. In order to compare values across different size tablets, the breaking strength is normalized for the area of the break. This normalized value, expressed in $kp/cm^2$, is sometimes referred in the art as tablet tensile strength. See Leiberman et al., *Pharmaceutical Dosage Forms—Tablets*, Volume 2, $2^{nd}$ ed., Marcel Dekker Inc., 1990, pp. 213–217, 327–329.

A sufficient amount of energy is applied to the tablet for a sufficient amount of time to decrease its hardness by at least about 20%, preferably about 20 to 80%. Preferably, the final hardness of the tablet is less than about 15 $kp/cm^2$, preferably about 1 to 8 $kp/cm^2$, more preferably about 2 to 6 $kp/cm^2$. Applicants have also observed an increase in tablet thickness of at least about 1%, preferably about 1 to 20%, after the application of energy.

Preferably, energy is applied to the tablet in the form of heat or electromagnetic radiation, such as microwaves. More preferably, energy is applied in the form of heat. Depending on the composition of the tablet, heating may be performed at a temperature generally in the range of ambient temperature to 100° C. or beyond for a time sufficient to achieve a softening effect.

Although applicants do not wish to be bound by theory, it is believed that the application of energy to the tablet releases the water of hydration from the excipient in the form of a hydrate. The excipient in the form of a hydrate then becomes only partially hydrated, while the water-swellable excipient becomes hydrated or swollen, thereby softening the tablet. Softening is achieved without the need for an external source of water. The present tablet can therefore advantageously be made using simple direct compression methods. The direct compression process enables the minimization or elimination of water-soluble, non-saccharide polymeric binders such as polyvinyl pyrrolidone, alginates, hydroxypropyl cellulose, hydroxypropylmethylcellulose, hydroxyethylcellulose, and the like, which can have an adverse effect on dissolution.

In a particularly preferred embodiment of the invention, the tablet is packaged between the tablet forming and energy application steps. That is, energy is applied to the tablet after the tablet is already in its package. In this manner, the tablet maintains a relatively low friability during handling and packaging operations. However, once in the package, it is softened to its final, chewable or disintegrative form for the consumer.

Specific embodiments of the present invention are illustrated by way of the following examples. This invention is not confined to the specific limitations set forth in these examples, but rather to the scope of the appended claims. Unless otherwise stated, the percentages and ratios given below are by weight.

EXAMPLES

Three batches of tablets were made using coated ibuprofen as the active ingredient. Batch A, according to the invention, also contained dextrose monohydrate and crospovidone. Batch B, also according to the invention, contained mannitol and crospovidone, while comparative Batch C contained dextrose monohydrate and sodium starch glycolate. The following table gives the ingredients and amounts (milligrams per tablet) for each batch.

|  | Batch A | Bartch B | Batch C |
|---|---|---|---|
| Sucralose | 8.0 | 8.0 | 8.0 |
| Coated Ibuprofen (69.0%) −30 mesh | 140.6 | 140.6 | 140.6 |
| Flavor | 10.0 | 10.0 | 10.0 |
| Dextrose Monohydrate USP | 850.0 |  | 850.0 |
| Mannitol |  | 850.0 |  |
| Crospovidone NF | 15.0 | 15.0 |  |
| Sodium Starch Glycolate |  |  | 15.0 |
| Magnesium Stearate NF | 7.5 | 7.5 | 7.5 |
| TOTAL | 1031.1 | 1031.1 | 1031.1 |

The tablets were compressed in a Betapress with 9/16" Biconcave tooling to a hardness of approximately 5–7 kp and a thickness of approximately 0.282" for Batches A and C and 0.313" for Batch B. The tablets were packaged in glass bottles with Teflon seal caps and placed on informal stability. The hardnesses and thicknesses were monitored at 2 and 4 hours at 60° C., and 1, 2, and 3 days at 50° C. The results were as follows:

| Condition | Batch A Hardness (kp) | Batch A Thickness (inches) | Batch B Hardness (kp) | Batch B Thickness (inches) | Batch C[1] Hardness (kp) | Batch C Thickness (inches) |
|---|---|---|---|---|---|---|
| Initial | 4.5–6.3 | 0.282–0.284 | 6.2–6.6 | 0.312–0.314 | 6.3–7.3 | 0.282–0.283 |
| 2 hr 60° C. | 2.2–2.6 | 0.300–0.302 | 6.1–7.7 | 0.315–0.317 | 5.9–6.5 | 0.288–0.290 |
| 4 hr 60° C. | 1.8–2.3 | 0.309–0.310 | 7.0–7.6 | 0.315–0.317 | 4.9–6.7 | 0.289–0.290 |
| 1 day 50° C. | 1.8–2.9 | 0.301–0.304 | 7.5–8.1 | 0.315–0.316 | 4.5–5.8 | 0.286–0.287 |
| 2 days 50° C. | 1.5–1.7 | 0.307–0.309 | 6.7–7.5 | 0.315–0.316 | 4.8–6.9 | 0.287–0.289 |
| 3 days 50° C. | 1.5–1.8 | 0.309–0.312 | 6.6–6.7 | 0.317–0.318 | 6.4–7.1 | 0.287–0.288 |

[1]Some hardening was observed after 3 days of heating, probably due to suboptimization of the formulation.

Batches A and C resulted in softer tablets, while Batch B did not.

[1] Some hardening was observed after 3 days of heating, probably due to suboptimization of the formulation.

We claim:

1. A tablet comprising: a) a pharmaceutically active ingredient, b) dextrose monohydrate, and c) crospovidone.

2. The tablet of claim 1 having a hardness of less than about 15 kp/cm².

3. A process for preparing a chewable or disintegrative tablet, comprising forming a tablet having a friability of less than about 2% from a mixture comprising a pharmaceutically active ingredient, an excipient in the form of a hydrate, and a water-swellable excipient, and then applying sufficient heat to the tablet for a sufficient time to decrease the hardness of the tablet by at least about 20%.

4. The process of claim 3, wherein the tablet is formed by direct compression.

5. The process of claim 3 wherein the tablet has a final hardness of less than about 15 kp/cm².

6. The process of claim 3, wherein the friability is less than about 1% and the tablet has a final hardness in the range of about 1–8 kp/cm².

7. The process of claim 3, wherein prior to application of heat to the tablet, the tablet is packaged.

8. The process of claim 3, wherein the active ingredient is selected from the group consisting of acetaminophen, ibuprofen, pseudoephedrine, dextromethorphan, diphenhydramine, chlorpheniramine, calcium carbonate, magnesium hydroxide, magnesium carbonate, magnesium oxide, aluminum hydroxide, mixtures thereof, and pharmaceutically acceptable salts thereof.

9. The process of claim 3, wherein the excipient in the form of a hydrate is selected from the group consisting of dextrose monohydrate, maltodextrinhydrate, lactose monohydrate, dextrinhydrate, citric acid monohydrate, dibasic calcium phosphate dihydrate, dibasic sodium phosphate dihydrate, dibasic sodium phosphate heptahydrate, dibasic sodium phosphate dodecahydrate, monobasic sodium phosphate monohydrate, and monobasic sodium phosphate dihydrate.

10. The process of claim 3, wherein the water-swellable excipient is selected from the group consisting of sodium starch glycolate, crospovidone, croscarmellose, microcrystalline cellulose, starches, and alginic acid.

11. The process of claim 3, wherein the tablet contains about 5 to about 90% by weight of excipient in the form of a hydrate based on the total weight of the tablet.

12. The process of claim 3, wherein the tablet contains about 0.1 to about 5% by weight of water-swellable excipient based on the total weight of the tablet.

13. The process of claim 3 wherein the excipient in the form of a hydrate functions as a direct compression filler.

14. A tablet produced by the process of claim 3.

* * * * *